(12) United States Patent
Calderon et al.

(10) Patent No.: US 9,833,606 B2
(45) Date of Patent: Dec. 5, 2017

(54) NON-REOPENABLE FLOW CONTROL CLAMP

(71) Applicant: Fenwal, Inc., Lake Zurich, IL (US)

(72) Inventors: Carlos Calderon, Waukegan, IL (US); Richard West, Lake Villa, IL (US); Bryan Blickhan, Libertyville, IL (US); Daniel Lynn, Spring Grove, IL (US); Arthur Kaganovsky, Lake Zurich, IL (US)

(73) Assignee: Fenwal, Inc., Lake Zurich, IL (US)

( * ) Notice: Subject to any disclaimer, the term of this patent is extended or adjusted under 35 U.S.C. 154(b) by 183 days.

(21) Appl. No.: 13/797,025

(22) Filed: Mar. 12, 2013

(65) Prior Publication Data

US 2014/0074047 A1 Mar. 13, 2014

Related U.S. Application Data

(60) Provisional application No. 61/698,398, filed on Sep. 7, 2012.

(51) Int. Cl.
*A61M 5/00* (2006.01)
*A61M 39/28* (2006.01)

(52) U.S. Cl.
CPC .................. *A61M 39/28* (2013.01)

(58) Field of Classification Search
CPC .... A61M 39/284; A61M 39/29; A61M 39/28; F16K 7/063; F16K 31/00
USPC ............................................ 604/250; 251/10
See application file for complete search history.

(56) References Cited

U.S. PATENT DOCUMENTS

| | | |
|---|---|---|
| 2,722,932 A | 11/1955 | Hickey |
| 2,908,476 A | 10/1959 | Hidding |
| 2,950,716 A | 8/1960 | Walter et al. |
| 3,127,892 A | 4/1964 | Bellamy, Jr. et al. |
| 3,942,228 A | 3/1976 | Buckman et al. |
| 4,038,726 A | 8/1977 | Takabayashi |
| 4,053,135 A | 10/1977 | Saliaris |
| 4,097,020 A | 6/1978 | Sussman |
| 4,193,174 A | 3/1980 | Stephens |
| 4,235,412 A | 11/1980 | Rath et al. |
| 4,247,076 A | 1/1981 | Larkin |
| 4,453,295 A | 6/1984 | Laszczower |
| 4,589,626 A | 5/1986 | Kurtz et al. |

(Continued)

FOREIGN PATENT DOCUMENTS

| | | |
|---|---|---|
| EP | 0206997 | 12/1986 |
| EP | 0691139 A1 | 1/1996 |

(Continued)

OTHER PUBLICATIONS

International Search Report for PCT/US03/01758 dated Jun. 23, 2003.

(Continued)

*Primary Examiner* — Kevin C Sirmons
*Assistant Examiner* — Tiffany Legette-Thompson
(74) *Attorney, Agent, or Firm* — Cook Alex Ltd.

(57) ABSTRACT

The present disclosure relates to clamps for controlling the flow of liquid through a fluid circuit. More particularly, the present disclosure relates to flow control clamps that can be substantially irreversibly secured in a closed position, thereby preventing reopening of the flow path of the tube and providing a sterile closure.

22 Claims, 4 Drawing Sheets

(56) References Cited

U.S. PATENT DOCUMENTS

| | | |
|---|---|---|
| 4,643,389 A | 2/1987 | Elson et al. |
| 4,676,476 A | 6/1987 | Herrli |
| 4,725,269 A | 2/1988 | Danby et al. |
| 4,764,996 A | 8/1988 | Pino |
| 4,807,622 A | 2/1989 | Ohkaka et al. |
| 4,835,824 A | 6/1989 | Durham et al. |
| 4,857,274 A | 8/1989 | Simon |
| 4,988,355 A | 1/1991 | Leveen et al. |
| 5,035,399 A | 7/1991 | Rantanen-Lee |
| 5,062,846 A | 11/1991 | Oh et al. |
| 5,167,656 A | 12/1992 | Lynn |
| 5,203,056 A | 4/1993 | Funk et al. |
| 5,226,892 A | 7/1993 | Boswell |
| 5,238,218 A | 8/1993 | Mackal |
| 5,270,003 A | 12/1993 | Bernes et al. |
| 5,416,954 A | 5/1995 | Sobin |
| 5,615,965 A | 4/1997 | Saurat et al. |
| 5,651,766 A | 7/1997 | Kingsley et al. |
| 5,702,383 A | 12/1997 | Giesler et al. |
| 5,817,116 A | 10/1998 | Takahashi et al. |
| 5,827,306 A | 10/1998 | Yoon |
| 5,836,619 A | 11/1998 | Shemesh et al. |
| 5,928,166 A | 7/1999 | Shemesh et al. |
| 6,089,527 A | 7/2000 | Utterberg |
| 6,113,062 A * | 9/2000 | Schnell ............... A61M 39/284 251/10 |
| 6,123,859 A | 9/2000 | Lee et al. |
| 6,126,618 A | 10/2000 | Bischof |
| 6,132,407 A | 10/2000 | Genese et al. |
| 6,161,812 A | 12/2000 | Guala et al. |
| 6,193,675 B1 | 2/2001 | Kraus et al. |
| 6,234,448 B1 | 5/2001 | Porat |
| 6,238,377 B1 | 5/2001 | Liu |
| 6,298,526 B1 | 10/2001 | Baumdicker et al. |
| 6,328,726 B1 | 12/2001 | Ishida et al. |
| 6,387,086 B2 | 5/2002 | Mathias et al. |
| 6,553,632 B1 | 4/2003 | Brumpton |
| 6,592,613 B1 | 7/2003 | Ishida |
| 6,626,884 B1 | 9/2003 | Dillon et al. |
| 6,638,282 B2 | 10/2003 | Ramsey |
| 6,644,618 B1 | 11/2003 | Balbo |
| 6,692,479 B2 | 2/2004 | Kraus et al. |
| 6,708,931 B2 | 3/2004 | Miura |
| 6,730,071 B1 | 5/2004 | Dassa |
| 6,742,760 B2 | 6/2004 | Blickhan et al. |
| 6,923,792 B2 | 8/2005 | Staid et al. |
| 7,044,941 B2 | 5/2006 | Mathias et al. |
| 7,087,047 B2 | 8/2006 | Kraus et al. |
| 7,137,611 B2 | 11/2006 | Aulicino |
| 7,384,416 B2 | 6/2008 | Goudaliez et al. |
| 7,766,854 B2 | 8/2010 | Goudaliez et al. |
| RE43,283 E | 3/2012 | Ishida |
| RE43,310 E | 4/2012 | Ishida |
| 8,262,639 B2 | 9/2012 | Mathias et al. |
| 2004/0106890 A1 | 6/2004 | Goudaliez et al. |
| 2005/0038374 A1 | 2/2005 | Williams, Jr. et al. |
| 2005/0107765 A1 | 5/2005 | Kashmiran et al. |
| 2005/0171492 A1 | 8/2005 | Rodriquez |
| 2005/0215975 A1 | 9/2005 | Mathias et al. |
| 2006/0015074 A1 | 1/2006 | Lynn |
| 2006/0129170 A1 | 6/2006 | Royce et al. |
| 2007/0007208 A1 | 1/2007 | Brugger et al. |
| 2007/0161978 A1 | 7/2007 | Fedenia et al. |
| 2007/0219513 A1 | 9/2007 | Lina et al. |
| 2007/0261214 A1 | 11/2007 | Nerbonne et al. |
| 2008/0132875 A1 | 6/2008 | Goudaliez |
| 2009/0306619 A1 | 12/2009 | Mathias et al. |
| 2010/0152681 A1* | 6/2010 | Mathias ............... F16K 7/063 604/250 |
| 2010/0168680 A1* | 7/2010 | Callahan ............ A61M 39/286 604/250 |
| 2012/0172755 A1 | 7/2012 | Mathias et al. |

FOREIGN PATENT DOCUMENTS

| | | |
|---|---|---|
| EP | 0799627 | 10/1997 |
| EP | 1000633 | 5/2000 |
| EP | 1064959 | 1/2001 |
| EP | 1125596 | 8/2001 |
| EP | 1389473 A1 | 2/2004 |
| EP | 03703927 | 3/2005 |
| WO | WO 93/25143 | 12/1993 |
| WO | WO 00/77428 A2 | 12/2000 |
| WO | WO 01/08582 A1 | 2/2001 |
| WO | WO 03/063945 A1 | 8/2003 |
| WO | WO 2007/112500 | 10/2007 |
| WO | WO 2007/133291 | 11/2007 |

OTHER PUBLICATIONS

Supplemental International Search Report for EP 03703927 dated Mar. 30, 2005.

Extended European Search Report and Opinion for EP 09015333 dated Jun. 30, 2010.

Extended European Search Report for EP Application No. EP 10 009215.

Photographs of Baxter "All in One Container" and Instruction Sheet dated Sep. 2011.

\* cited by examiner

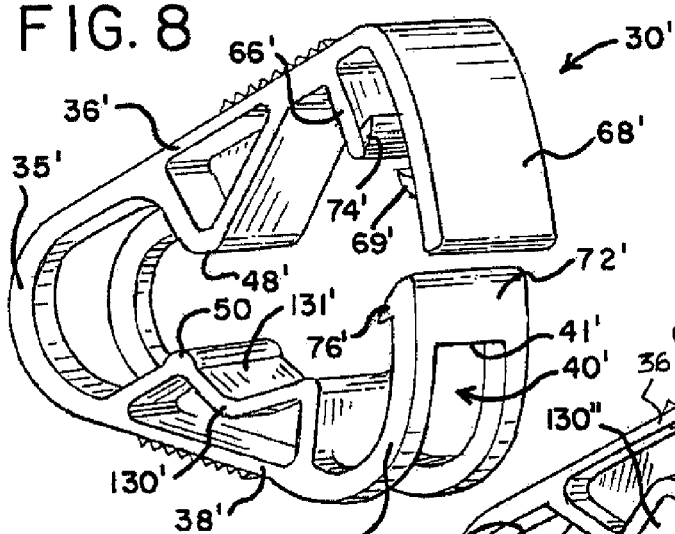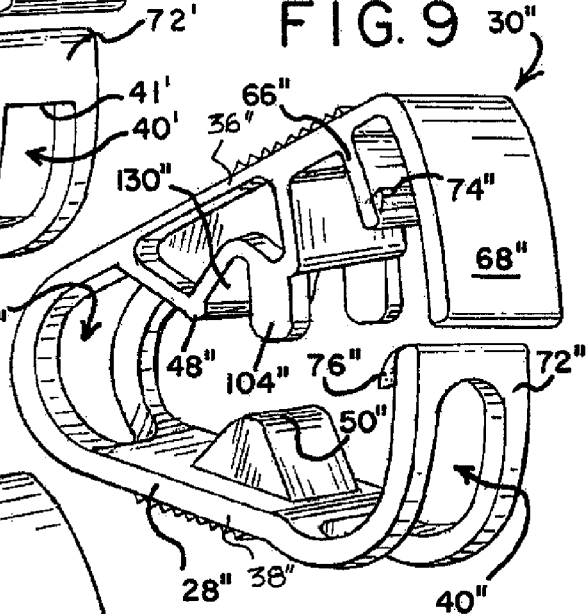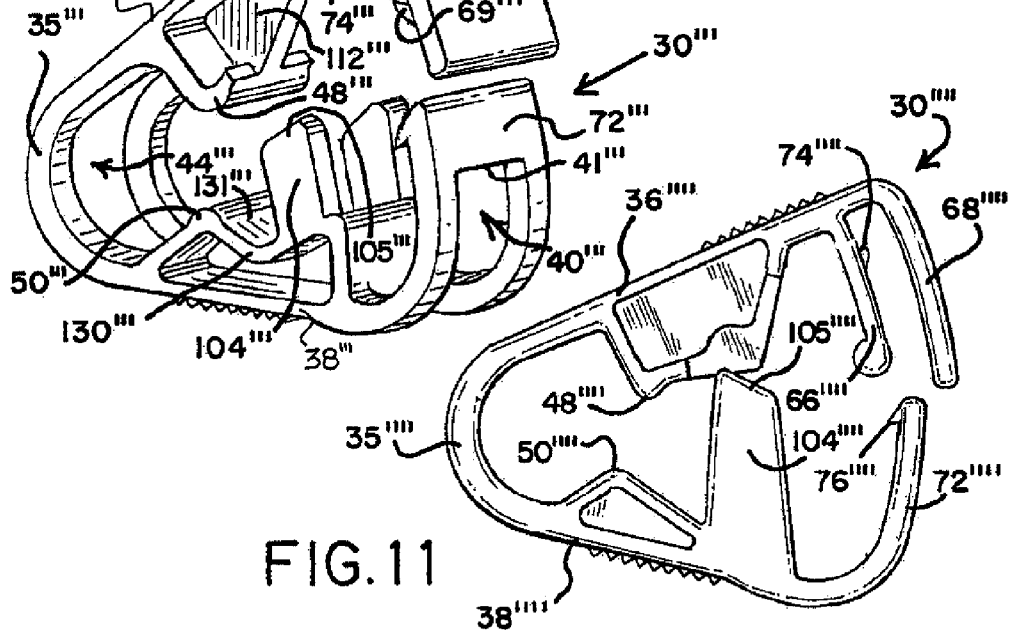

NON-REOPENABLE FLOW CONTROL CLAMP

CROSS-REFERENCE TO RELATED APPLICATIONS

This application claims the benefit of U.S. Provisional Patent Application Ser. No. 61/698,398 filed Sep. 7, 2012, the contents of which is incorporated herein by reference in its entirety.

FIELD OF THE DISCLOSURE

The present disclosure is directed to flow control clamps such as those commonly used in the medical field. More particularly, the present disclosure is directed to flow control clamps that are used to restrict flow through a plastic tube defining a flow path. Even more particularly, the present disclosure is directed to flow control clamps that once closed, irreversibly restrict flow and cannot be reopened without using extraordinary means and/or destroying the clamp. The present disclosure is also directed to fluid processing sets that include one or more sterile closures such as the clamps described herein

BACKGROUND

A disposable plastic container and tubing set or fluid circuit is typically used for collecting blood from a donor. The disposable blood collection set includes a venipuncture needle for insertion into the arm of the donor. The needle is attached to one end of a flexible plastic tube which provides a flow path for the blood. The other end of the plastic tube is attached to one or more plastic bags or containers for collecting the withdrawn blood.

The blood collection set may also include a sampling sub-unit. The sampling sub-unit allows for collection of a sample of blood, which sample can be used for testing of the blood. Preferably, the sample is obtained prior to the "main" collection of blood. Collecting the sample prior to the main collection reduces the risk that bacteria residing on the donor's skin where the needle is inserted (i.e., in particular, the small section of detached skin commonly referred to as the "skin plug") will enter the collection container and contaminate the blood collected for transfusion. Thus, it is preferred that the blood sample, which may include the skin plug, be diverted from the main collection container.

An example of a blood collection set with such a "pre-donation" sampling sub-unit is described in U.S. Pat. Nos. 6,387,086 and 6,520,948, which are incorporated by reference herein. The collection sets described therein include a needle and a length of tubing, one end of which is attached to the needle and the other end of which is attached to one or more collection containers. The tubing set also includes an additional line which is branched from the main line at a Y-connection site in the tubing set. The branched line is attached to a sampling pouch for collecting a smaller volume of blood from which samples may be obtained.

The sampling sub-unit may further include a pre-attached holder for receiving blood sample vials or tubes. The holder is connected to the outlet port of the sampling pouch and includes a needle in the holder interior. When the blood sample vial is inserted into the holder, the needle pierces the rubber cap (septum) of the vial and blood from the sampling pouch is drawn into the vial. The blood-filled vial is removed from the holder and the procedure may be repeated with as many vials as required.

The blood collection set described above also includes flow control clamps for controlling the flow of biological fluid (e.g., blood) through the set and to the sampling pouch and/or collection container. Flow control clamps commonly used are the Roberts-type clamps, which are well known in the art. The Roberts-type clamps are placed on the tubing line leading to the blood collection container and on the tubing line leading to the sampling pouch. A Roberts-type clamp is typically made from a molded piece of plastic. The clamp typically includes two "legs" which are adapted to engage each other in a snap-fit, spring relation. The body of the clamp includes a pair of apertures through which the tubing passes. The clamp further includes a pair of projections or tube contacting members which compress the tubing when the body of the clamp is depressed, thereby restricting flow through the tube. Clamps of this type are generally described in U.S. Pat. Nos. 3,942,228, 6,089,527 and 6,113,062, all of which are incorporated herein by reference.

The clamps described in these patents also typically include locking mechanisms for locking the legs together and release means which, when actuated by the technician, disengages the locked legs of the flow control clamp. Disengagement of the ends decompresses the tube and permits fluid flow through the flow path. Thus, by selectively opening and closing the different flow paths (by depressing or releasing the clamps), the technician can control the flow of blood from the donor, diverting the blood to the desired container or sampling pouch, as necessary.

In certain instances, however, it may not be desirable to reopen a closed flow path. This may particularly be the case when drawing blood samples from the sampling pouch into sample vials. For example, when the sampling pouch is filled with the required or desired volume of blood (for sampling), the line from the donor to the pouch is typically closed by the Roberts-type clamp, and remains closed as the sampling vials are filled. After clamping the sampling line closed, technicians are further instructed to more permanently seal the line using metal clips and/or by heat-sealing the line in ways that will be known to those in the field. Sealing the sampling line substantially ensures that airborne bacteria or other contaminants that may enter the set through the sampling sub-unit do not contaminate the remainder of the set, including the needle and tube leading to the collection container. In short, the clips or heat seal provide a sterile barrier to the remainder of the set.

Unfortunately, on occasion, prior to permanently sealing the sampling line, some technicians have been known to unclamp the sampling line in order to draw additional blood into the pouch so that additional sample vials may be filled. However, by doing so, the system becomes "open" and contaminants introduced from the outside environment may enter the system. Traditional Roberts-type clamps (as well as other commercially available clamps) are readily and easily openable and do not provide a disincentive to drawing additional blood into the sampling pouch.

More recently, non-reopenable clamps have become available to protect against re-opening of the clamp and the tubing flow path engaged by the clamp. Examples of such non-reopenable clamps are disclosed in U.S. patent application Ser. No. 12/635,440, filed Dec. 10, 2009, now U.S. Pat. No. 8,262,639 and U.S. Patent Application Publication No., the 20090306619, the entire contents of each is incorporated herein by reference. While the non-reopenable clamps described therein, as well as other non-reopenable clamps, have worked satisfactorily, efforts continue to develop and provide easy-to-use, low cost, non-reopenable flow control devices that are or can provide a sterile closure.

SUMMARY

In one aspect, the present disclosure is directed to a device for controlling flow through a fluid circuit. The device includes a flexible body having a central portion and first and second relatively movable legs extending from the central portion. The central portion includes a window for receiving flexible tubing therethrough. The first and second legs are relatively movable from a spaced apart position to a closed position. One of the first and second relatively movable legs includes at least a pair of substantially parallel terminal arms extending therefrom with the arms defining a gap therebetween. The other of the first and second relatively movable legs includes a single terminal arm that extends therefrom. One of the pair of substantially parallel terminal arms includes a tooth that includes an engagement surface for engaging a tooth on the single terminal arm. The engagement surface and a surface of the one of the pair of substantially parallel terminal arms from which the tooth extends forms an angle of 90° or less. The single terminal arm of the other of the first and second legs includes a tooth that has an engagement surface that forms an angle of 90° or less with the surface of the single terminal arm from which the tooth on the single arm extends. One of the first and second legs carries both (a) tube contacting member for compressing the flexible tube when the first and second legs are in the closed position and (b) a ramp adjacent to the tube contacting member on the one of said first and second legs, the ramp including an ascending and descending surface.

In another aspect, the present disclosure is directed to a fluid processing set. The set includes a container adapted for receiving biological fluid from a donor, a donor access device and a tubing segment which defines a flow path that is in flow communication with the container and the access device. The set further includes a flow control device associated with the tubing segment. The flow control device includes a flexible body having a central portion and first and second legs extending from the central portion. The central portion includes a window for receiving flexible tubing therethrough. The first and second legs are movable from a spaced apart position to a closed position. One of the first and second legs includes at least a pair of substantially parallel terminal arms extending therefrom and defining a gap therebetween. The other of the first and second legs includes a single terminal arm that extends therefrom. One of the pair of substantially parallel arms includes a tooth that has an engagement surface for engaging a surface on a tooth on the single terminal arm. The engagement surface forms an angle of 90° or less with the surface of the one of the pair of generally parallel arms from which the tooth extends. The single arm of the other of said first and second legs includes a tooth that faces the engagement surface of the tooth on the one of the pair of generally parallel terminal arms in the closed position and has an engagement surface that forms an angle of 90° or less with the surface of the single terminal arm from which the tooth on the single arm extends. A tube contacting member id carried by one of the first and second legs for clamping the flexible tubing when the first and second legs are in the closed position. The other of the first and second legs carries both (a) tube contacting member for compressing the flexible tube when the first and second legs are in the closed position and (b) a ramp adjacent to the tube contacting member on the other of said first and second legs, the ramp including an ascending and descending surface.

BRIEF DESCRIPTION OF THE FIGURES

FIG. 8 is a perspective view of an alternative embodiment of the flow control device disclosed herein;

FIG. 9 is a perspective view of another alternative embodiment of the flow control device as disclosed herein;

FIG. 10 is a perspective view of still another alternative embodiment of the flow control device as disclosed herein; and FIG. 11 is a side view of another alternative embodiment of the flow control clamp as disclosed herein.

DETAILED DESCRIPTION

Figure 1:
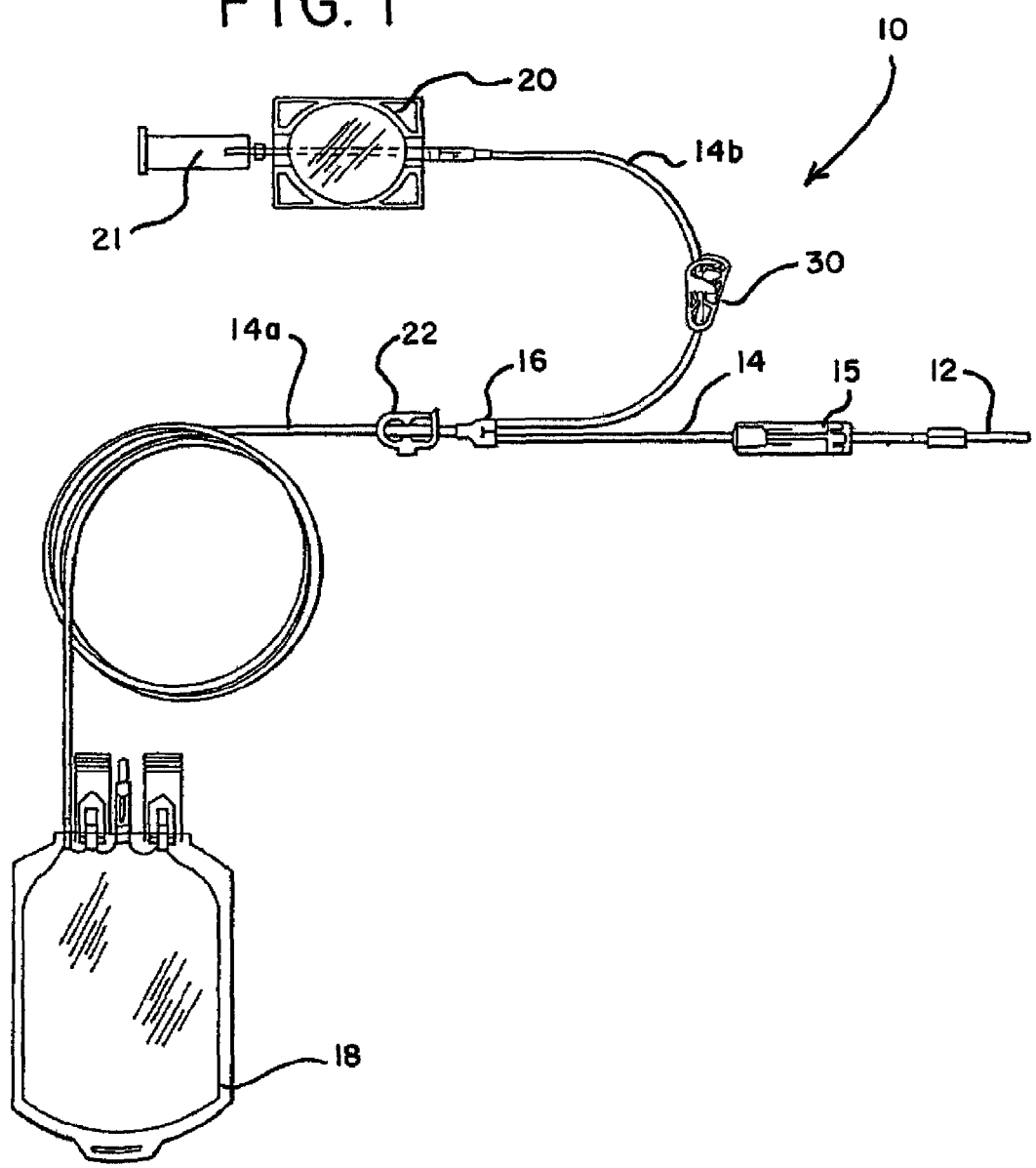
FIG. 1 is a plan view of a blood tubing set including a flow control clamp as disclosed herein.

With reference to the drawings, FIG. 1 depicts a blood collection set 10 of known type that is used in the collection of blood from a donor. Tubing set 10 includes a venipuncture needle 12 and a length of tubing 14. Tubing 14 branches at for example, Y-connector 16 into tubing segment 14a and tubing segment 14b. Tubing segment 14a provides a flow path to a collection container 18 and tubing segment 14b provides a flow path to a second container, such as, a sampling pouch 20. The sampling pouch may also include a holder 21 for receiving a blood sampling vial or tube. (Also shown is a needle protector 15 for storing the needle after use.)

In the blood tubing sets of the type shown in FIG. 1, tubing segments 14a and 14b are passed through flow control clamps 22 and 30 which may be a standard Roberts-type clamp and an irreversibly closable or non-reopenable flow control device as disclosed herein. The terms "irreversibly" closed or non-reopenable refer to a flow control device that once in the closed position is not readily releasable from the closed position in the normal and intended mode of operation. An "irreversibly" closed or non-reopenable control device can only be released from the closed and locked position by extraordinary and unintended manipulation of the clamp, including breakage of the clamp. A flow control clamp that is "irreversibly" closed or non-reopenable restricts flow through the flow path that extends through the clamp and does not allow for flow to be re-established without extraordinary or unintended manipulation, including destruction of the clamp. A flow control clamp that is "irreversibly" closed or closable includes no release members such as, but not limited to, the release members described in U.S. Pat. Nos. 3,942,228, 6,089,527, 6,113,062.

Thus, for example, whereas flow control clamp 22 (e.g., a standard Roberts-type clamp) can be selectively opened and closed, as desired, device 30, which is the subject of the present disclosure, once closed, remains irreversibly closed or non-reopenable, as set forth above. Alternatively, both clamps 22 and 30 may be non-reopenable clamps of the type described herein.

Figure 2:
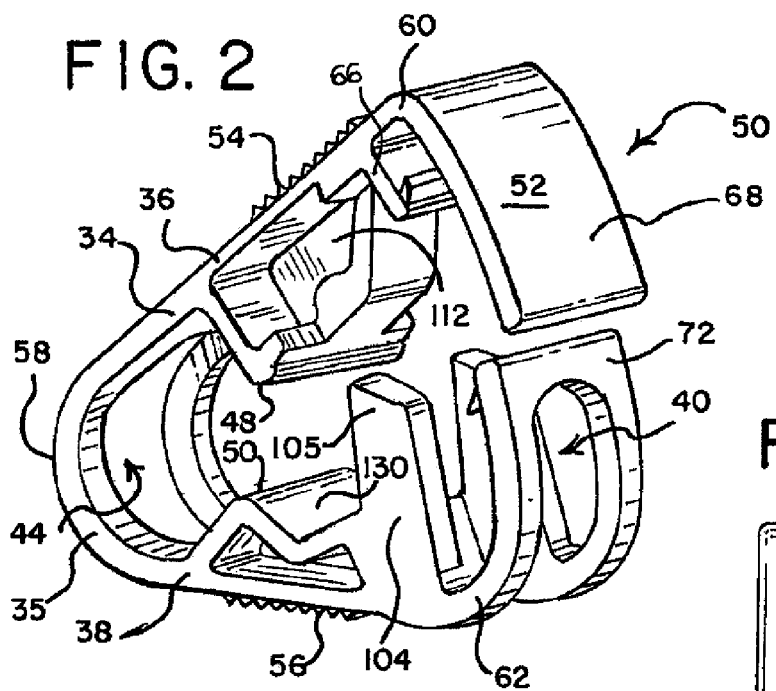
FIG. 2 is a perspective view of a flow control device as disclosed herein.

Turning now to FIG. 2, flow control device 30 of the present disclosure includes a generally curved, bent or otherwise non-linear body 34 (described in more detail below). Preferably, flow control clamp 30 may be made of any flexible, moldable, plastic material that can be steam sterilized. In addition, flow control clamp 30 and body 34 should be made of a material that is strong, yet sufficiently flexible so that the clamp can be flexed and squeezed by the technician without breaking. Examples of suitable materials are many of the known plastic materials typically used in the medical field, including, but not limited to polyoxymethylene and polypropylene. Most preferred of the above-identified materials is polyoxymethylene, such as the polyoxymethylene known as Hostaform™ available from Ticona, of Frankfurt, Germany. In addition, other materials that can be sterilized by other forms of sterilization, such as gamma sterilization, may also be used. One such material is a terpolymer of acrylonitrile, butadiene and styrene (ABS). In addition, some grades of polyester (PET and PBT) may be suitable (and which may be sterilized by radiation and steam). PETG may likewise be suitable. Also, alloys of polyester and polycarbonate with other polymers (such as polycarbonate/polyester) may be used. HDPE, which may be suitable for radiation sterilization can be used and some grades of inorganically filled HPDE may also be suitable.

Figure 3:
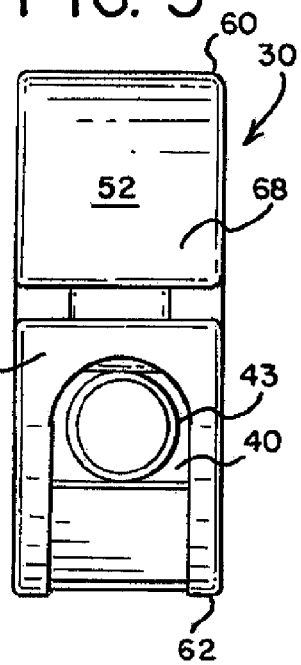
FIG. 3 is an end view of the flow control device of FIG. 2.
Figure 3A:
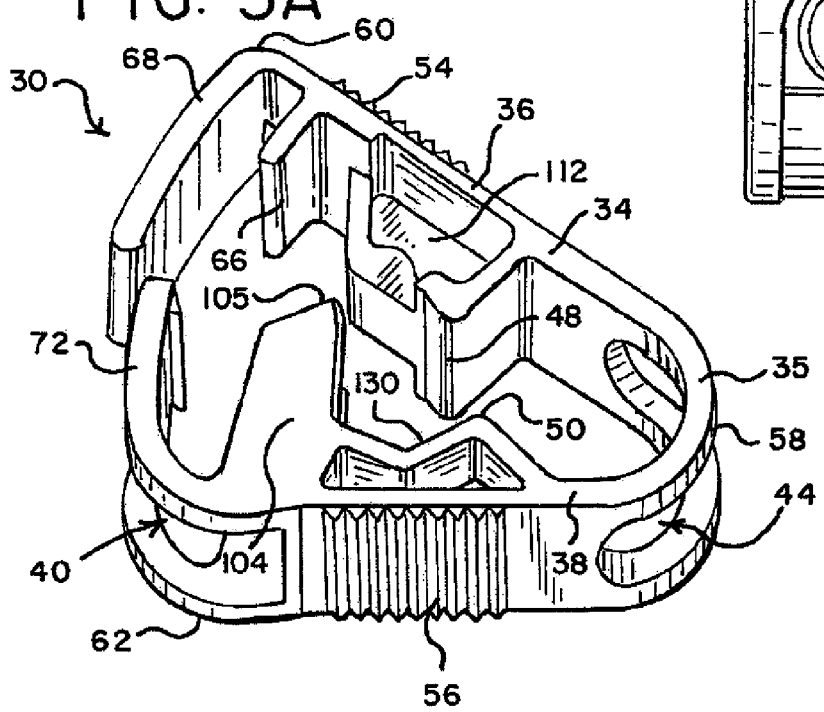
FIG. 3A is another perspective view of the flow control device of FIGS. 2 and 3.
Figure 4:
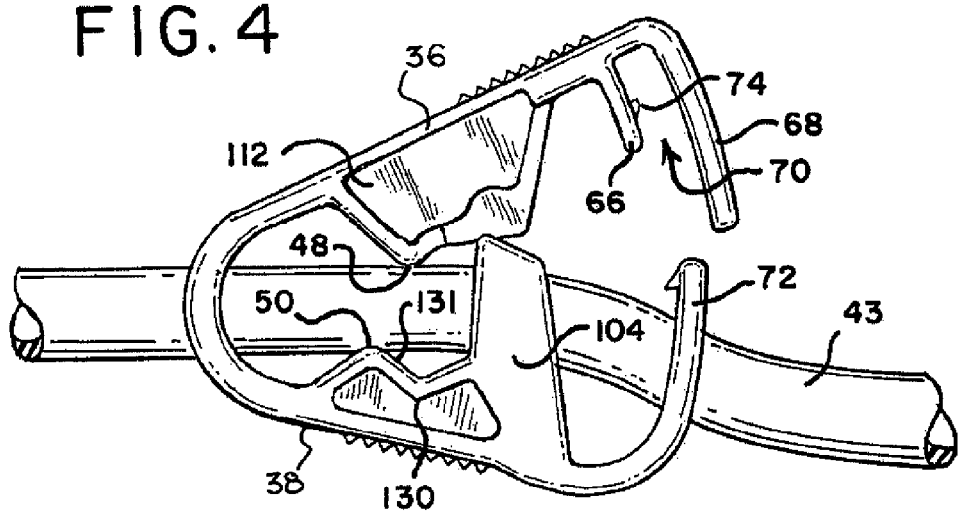
FIG. 4 is a plan view of the flow control device of FIG. 2 in an open position.
Figure 5:
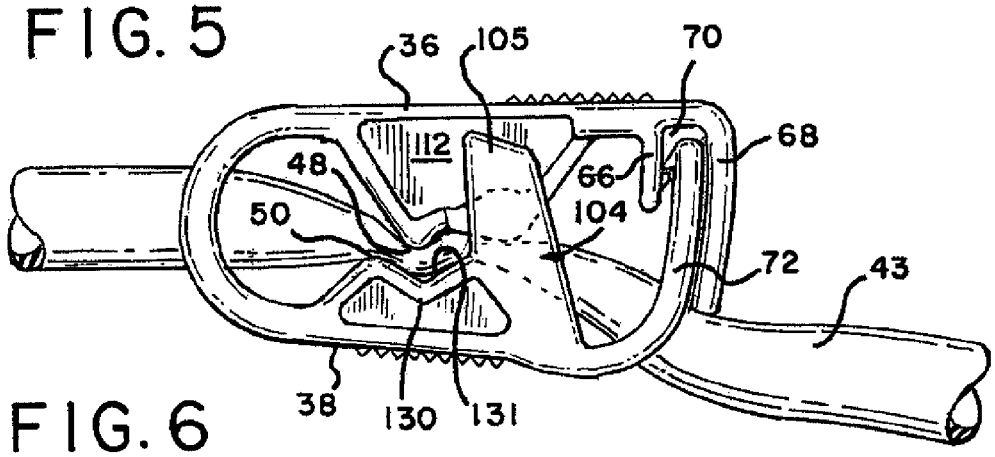
FIG. 5 is a plan view of the flow control device of FIG. 2 and tubing with the device in the irreversibly closed, non-reopenable position.

As further shown in FIGS. 2 and 3A, flow control device such as clamp 30 includes body 34 that has a central portion 35 and two legs 36 and 38 extending therefrom. Legs 36 and 38 are preferably disposed in a generally facing relationship relative to each other. Legs 36 and 38 are initially in a spaced apart position as shown in FIGS. 2, 3A and 4, and are movable from the first open spaced apart position toward each other to ultimately a second irreversibly closed or locked position as shown in FIG. 5. Legs 36 and 38 should be sufficiently spaced apart to allow for uninhibited threading of tubing 43 through said clamp 30 (as generally shown in FIG. 3). Preferably, central portion 35 serves as a hinge or more particularly, a living hinge that facilitates movement of legs 36 and 38 toward each other.

Clamp body 34 further includes apertures or windows 40 and 44 for receiving a length of plastic tubing therethrough. In the illustrated embodiment, aperture or window 44 is defined within the central portion 35 of body 30 and window 40 is defined in leg 38; however, it will be appreciated that the window may be defined in leg 36 or by a combination of the legs. In one embodiment, as shown in FIG. 2, apertures 40 and 44 are preferably circular or oval-like although, as discussed below and shown in FIGS. 8 and 10, at least one of windows, e.g., 40 may have a different geometry where window 40 also provides an engagement surface for a tooth, barb or other engagement mechanism. As shown in FIGS. 2 and 3A, windows 40 and 44 are entirely contained within body 34 of flow control clamp 30. Thus, when a length of tubing 43 is inserted through windows 40 and 44, the rim defining the window completely encloses and surrounds the tubing at the point where the tubing extends through the apertures.

Also, it may be desirable (but not necessary) that apertures 40 and 44 be generally aligned with each other and not substantially offset relative to one another. This provides, among other things, for easier threading of the length of tubing 43. Where a more tortuous path for the tubing is desired (e.g., to limit relative movement of clamp 30 and the plastic tubing 43), windows 40 and 44 need not be substantially aligned. In an alternative embodiment, windows 40 and 44 need not completely surround the tube, but instead may include lateral slots, as described, for example, in U.S. Pat. No. 6,113,062. The lateral slots extend to the outer edge of the body so that during insertion of the tube, the clamp can be laterally slipped on the tube (as opposed to threading).

As shown in FIGS. 2 and 3A, flow control clamp 30 includes one or more tube contacting members 48 and 50. Tube contacting members 48 and 50 are carried by legs 36 and 38, respectively. As shown in FIGS. 2 and 3A, tube contacting members 48 and 50 may be teeth-like projections which compress the tubing when the clamp is closed. Alternatively, tube contacting members 48 and 50 may simply be blunt, oppositely facing surfaces. Although two generally oppositely facing contacting members are shown in FIGS. 2 and 3A and are preferred, it will be understood that flow control clamp 30 of the present disclosure may include only one tube contacting member carried by one of the legs 36 or 38 or multiple tube contacting members on each of legs 36 and 38.

The outer surface 52 of flow control clamp 30 is generally flat and smooth. However, outer surface 52 may include portions that are roughened or textured to provide some friction when contacted by the fingertips of the technician during operation. As shown in FIGS. 2 and 3A, outer surface 52 of body 34 includes ribbed portions 54 and 56, which provide such a frictional surface for contacting by the fingers of the technician during closure and compression of flow control clamp 30.

As best shown in FIGS. 2 and 3A, flow control clamp 30 is substantially free of any sharp corners or edges. For example, bends 58, 60 and 62 in body 34 are not abrupt, sharp corners, but are gradually curved and rounded. In addition, edges 63 of body 34 are preferably rounded or beveled. A flow control clamp 30 that is substantially free of sharp corners and edges and is more rounded or beveled ensures that the flow control clamp will not puncture the packaging of blood processing sets, thereby maintaining sterility of the packaged set.

As discussed generally above, where the blood processing set includes a sampling pouch of the type shown in FIG. 1, it may be desirable to provide a flow control clamp 30 that provides an additional level of sterility maintenance by discouraging and/or even preventing the technician from reopening a previously closed clamp. This way, the sterility of the remainder of the blood processing set will be maintained and will not be compromised by bacteria from the outside environment and/or technicians will not have the option to unclamp sampling line 14b in order to draw additional blood into the pouch so that additional vials can be filled. Indeed, clamps 30 of the type described above, once in the closed, non-reopenable condition, maintain sterility of the system or the portion of the system beyond the clamp if the system on the other side of the clamp is opened or otherwise exposed to the outside environment. Thus, the closures and clamps described herein may be considered sterile closures in that they are airtight and watertight, able to withstand a pressure challenge of about 6 psi and/or are able to withstand a bacterial ingress challenge. The body of the clamp or closure should be strong enough to prevent any deformation created by the pressure challenge.

Accordingly, flow control clamp 30 includes a locking mechanism, and more particularly, legs 36 and 38 include surfaces that are adapted for irreversibly securing together legs 36 and 38 when the legs of flow control clamp 30 are moved from a first (spaced-apart) position to the second closed position, as shown in FIGS. 4 and 5 respectively. Legs 36 and 38 should have sufficient structural rigidity to maintain adequate compression of the tubing and be able to withstand air pressure challenge that would cause clamp 30 to deform and compromise the sterility of the system.

Many different ways for securing legs 36 and 38 together to prevent easy reopening by the technician are contemplated by the present disclosure. For example, flow control clamp 30 may include engagement members on the leg surfaces for interlocking legs or members 36 and 38. Specifically, as shown in FIGS. 4 and 5, each of the legs may terminate in or include at or near their terminal end portions one or more inwardly disposed members or arms. For example, leg 36 of flow control clamp 30 may include a pair of spaced-apart parallel arms 66 and 68 that depend or otherwise extend from leg 36 at or near a distal or terminal end portion of the clamp. Thus, as shown in FIGS. 2-11, leg 36 terminates in "outer" arm 68 and also carries "inner" arm 66 that is spaced from arm 68 but is still at or near the terminal end such that the pair of arms 66 and 68 are referred to as "terminal" arms." Leg 38 terminates in and carries arm 72 and spaced-apart arms 66 and 68 define a gap 70 for receiving a single terminal arm 72. It will be appreciated that the placement of arms 66 and 68 and arm 72 may be reversed such that parallel arms 66 and 68 may extend from leg 38 and single arm 72 may extend from leg 36.

As shown in FIGS. 2, 3A and 4-5, terminal arms 66 and 68 are spaced apart and preferably parallel to one another. Gap 70 defined by arms 66 and 68 should be sufficiently wide to receive terminal arm 72, as described in further detail below, but not so wide that single arm 72 can be moved outwardly and away from arm 66 such that arm 66 and arm 72 become disengaged.

As further shown in FIGS. 2, 3A, 4-6, "inner" arm 66 and "outer" arm 68 vary in length. Preferably, inner arm 66 is shorter than outer arm 68. A shorter inner arm 66 makes it more difficult to grasp by the technician (even using a tool) and less susceptible to non-reopening of clamp 30 than if arm 66 extended beyond tooth 74 in the direction of leg 38. One of the pair of spaced-apart arms 66 or 68 may further include a tooth 74 that projects into gap 70, while arm 72 includes a tooth 76 that projects toward the arm 66.

As legs 36 and 38 are moved from the first open spaced-apart position, as generally depicted in FIG. 4, to the second closed irreversibly locked position of FIG. 5, tube contacting members 48 and 50 compress the tube 43, thereby restricting flow therethrough. As flow control clamp 30 is compressed further, single arm 72 enters gap 70. As tooth 76 contacts tooth 74, arm 72 is slightly outwardly displaced until it clears tooth 74. Once clear of tooth 74, arm 72 snaps forward toward arm 66, and tooth 76 engages tooth 74 to effectively close and lock flow control clamp 30, such that it is non-reopenable. Tube contacting members 48 and 50 may cooperate to pinch tubing 43 therebetween or, more preferably, tube contacting member 48 may press tubing 43 against the surface 131 of ramp 130, as shown in FIG. 5.

Figure 6:
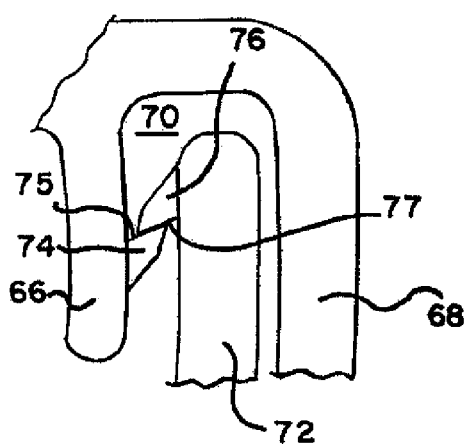
FIG. 6 is an enlarged view of the device of FIG. 5 showing the engagement of the teeth on the cooperating arms.
Figure 7:
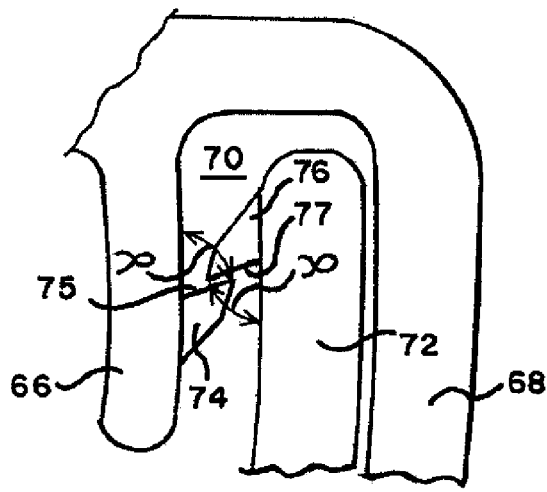
FIG. 7 is an enlarged view of the device in FIG. 4 in the open position showing the angle(s) of the teeth relative to the arms that carry them.

As further shown in FIGS. 6 and 7, tooth 74 includes an engagement surface 75 for engaging a corresponding engagement surface 77 of tooth 76. With respect to engagement surfaces 75 and 77, such surfaces, preferably form an angle α of no greater than 90° and preferably less than 90° with surfaces of arms 66 and 72 from which teeth 74 and 76 extend, as shown in FIG. 7. An angle α of less than 90° provides stronger engagement and an interlock between teeth 74 and 76, thereby making it more difficult to separate arms 66 and 72. In one embodiment, the angle α formed between engagement surfaces 75 and 77 (with their respective arms) may preferably be between 20°-90°. In addition, engagement surfaces may include a roughened or otherwise textured surface finish, or may include geometric structures such as serrated teeth or ribs to inhibit relative movement (e.g., sliding) of teeth 74 and 76.

Outer arm 68 prevents release or further outward displacement of arm 72 from the closed position, thereby making clamp 30 more capable of being "irreversibly closed" or non-reopenable. Outer arm 68 may be thicker and a less flexible than, for example, arm 66, thereby providing more strength to arm 68 and making it even more difficult to release extension 72. As will be appreciated by those in the field, flow control clamp 30 does not include any tabs or other means for readily releasing extension 72. Thus, flow control clamp 30 remains in the second closed position. In addition, clamp 30 lacks any easy-to-grasp surface or member that can be used to pry open the clamp when it is in the second closed position. For example, clamps that have tabs or outwardly extending members or surfaces may be more susceptible to re-opening by being grasped by a user or accidentally caught on an object and used as a lever arm to pry open the clamp. In contrast, the interengaging legs 36 and 38 including associated arms 66, 68 and 72, as described above, are contoured relative to each other and are in sufficiently close association so as to be devoid of any easy-to-grasp surface or member to allow grasping or other manipulation that could result in relatively easy re-opening of the clamp. Accordingly, the compact and contained body of clamp 30 prevents inadvertent or even intentional opening of the clamp once in the non-reopenable position.

As shown in FIGS. 2, 3A, 4 and 5-6, clamp 30 also preferably includes lateral and preferably parallel arms 104 that extend from the sides of leg 38. Lateral arms 104 may act as a guide for threading the tubing 43 through apertures 40 and 44 of clamp 30 and help maintain (e.g., center) the tubing within the clamp body and more specifically, between contacting members 48 and 50 and on ramp 130. In addition, arms 104 may prevent distortion of the clamp when in the closed position. It will be appreciated that arms 104 need not extend from the outermost surface of member 38; however, the arms should be spaced sufficiently apart such that tube 43 can freely pass between the arms without arms 104 substantially pressing against tubing 43 so as to, for example, restrict fluid flow through the tube. As shown in FIGS. 2 and 3A, leg or member 36 which carries tube contacting member 48 may further include a cutout 112 for receiving or otherwise accommodating distal end tip 105 of one or both lateral arms 104. In a preferred embodiment, contact members and ramps span the width of the leg with which it is associated.

FIGS. 8-11 show alternative embodiments of a clamp 30 (labeled 30', 30", 30''' and 30'''' and with prime numbers used to identify similar or common elements to the clamp elements depicted in FIGS. 2-7). As shown in FIGS. 9 and 10, clamps 30" and 30''' include parallel lateral arms 104" and 104'''. As shown in FIG. 9, lateral arms 104" may extend from ramp 130" (discussed in more detail below) downwardly from member 36. In FIG. 10, lateral arms 104''' may extend from ramp 130''' or tube contacting member 50''', also carried by "lower" leg 38'''. Also, as shown in FIG. 9, tube contacting member 50" does not span the entire width of leg 38 thereby allowing lateral arms 104''' to surround tube contacting member 50''' when clamp 30 is in the closed position.

As shown in FIGS. 8 and 10, "outer" arm 68' or 68''' may also include a tooth 69' or 69''' that projects from the surface of arm 68' or 68''' that faces gap 70. Tooth 69' or 69'''' may have the same geometry as teeth 74 and 76 previously described. Tooth 69' or 69''' may be adapted to engage the rim of window 40' or 40'''. In that regard, at least the rim 41' and 41''' of window 40' and window 40''' may be non-arcuate and preferably straight to provide an engagement surface for tooth 69' or 69'''.

As will be appreciated from the discussion above and the Figures, clamps of the type disclosed herein preferably include a ramp carried by one or both members 36 and 38. As shown in the Figures, ramps 130, 130', 130" or 130''' may be adjacent to one of the tube contacting members 48 and/or 50 and may often be adjacent to or integral with lateral arms 104, 104', 104" or 104'''. Ramps 130, 130', 130" or 130''' provide a surface(s) over which tubing 43 travels between windows 40 and 44. Ramps 130, 130', 130" or 130''' may include one or more ascending and descending surfaces such that when clamp 30 is in a closed position, the tubing is curved upwardly and/or downwardly as it approaches window 44. The tortuous path provided by ramps 130, 130', 130" or 130''' makes it more difficult for the tubing and clamp 30 to slide relative to one another when clamp 30 is in the irreversibly closed or non-reopenable condition. Ramps 130, 130', 130" or 130''' (as well as tube contacting members 48 and 50, 48' and 50', etc.) may also include a roughened or otherwise textured surface finish to further limit or prevent relative movement of clamp 30 and tubing 43.

FIG. 11 shows a clamp that includes a pair of lateral arms, but wherein arms 66"" and 68"" are of comparable length. Teeth 74"" and 76"" on arms 66"" and 68"" are angled and may be textured, as described above. In the clamp 30"" of FIG. 11, a ramp such as 104 may be optional.

It will be appreciated that the description set forth above has been offered for illustrative purposes only. Other embodiments and other modifications to the flow control clamp shown and described above will be readily apparent to one skilled in the art and may also be included within the scope of the present disclosure. The above description is not intended to limit the scope of the invention of this application, which is as defined in the claims below.

What is claimed is:

1. A flow control device comprising: a flexible body comprising a central portion and first and second relatively movable legs extending from said central portion, said central portion including a window for receiving flexible tubing therethrough, said first and second relatively movable legs being movable from a spaced apart position to a closed position; one of said first and second relatively movable legs comprising at least a pair of substantially parallel terminal arms extending therefrom, said arms defining a gap therebetween; the other of said first and second relatively movable legs comprising a single terminal arm extending therefrom; wherein one of said pair of substantially parallel terminal arms includes a tooth having an engagement surface for engaging a surface on a tooth on said single terminal arm, wherein said engagement surface and a surface of said one of said pair of substantially parallel terminal arms from which said tooth extends forms an angle α of less than 90°; and wherein said single terminal arm of said other of said first and second legs includes a tooth having an engagement surface that faces said engagement surface of said tooth on said one of said pair of substantially parallel terminal arms in said closed position, and wherein said engagement surface of said tooth on said single terminal arm and a surface of said single terminal arm from which said tooth of said single terminal arm extends forms an angle α of less than 90°; and wherein one of said first and second legs carries both (a) a tube contacting member for compressing the flexible tube when said first and second legs are in a closed position and (b) a ramp adjacent to said tube contacting member on said one of said first and second legs, said ramp comprising an ascending surface and a descending surface.

2. The flow control device of claim 1 wherein relative movement of said first and second legs from the spaced apart position to the closed position introduces said single terminal arm into said gap.

3. The flow control device of claim 1 further comprising a tube contacting member carried by said other of said first and second legs for compressing said flexible tubing between said contacting members when said first and second legs are in the closed position.

4. The flow control device of claim 1 wherein said ramp has a surface wherein at least a portion of said surface has a roughened or otherwise textured finish.

5. The flow control device of claim 1 wherein said first and second legs extending from said central portion have a width and said tube contacting member spanning said entire width of said first and second legs.

6. The flow control device of claim 1 wherein said flow control device is not readily releasable when secured in the closed position.

7. The flow control device of claim 1 wherein said flow control device is devoid of any surface or member to allow for grasping and re-opening of said device.

8. The flow control device of claim 1 wherein one of said pair of substantially parallel arms is shorter in length than the other of said pair of substantially parallel arms.

9. The flow control device of claim 8 wherein the shorter of said pair of substantially parallel terminal arms includes said tooth.

10. The flow control device of claim 8 wherein said other of said pair of substantially parallel terminal arms includes a tooth on a surface of said other of said pair of substantially parallel arms facing said gap.

11. The flow control device of claim 10 wherein said tooth on said other of said pair of substantially parallel terminal arms has an engagement surface that forms an angle α with the surface of a longer of said pair of substantially parallel terminal arms from which said tooth extends that is less than 90°.

12. The flow control device of claim 1 wherein said single terminal arm comprises a window for receiving the flexible tubing therethrough.

13. The flow control device of claim 12 wherein said windows are completely enclosed by said body.

14. The flow control device of claim 12 wherein said window in said single terminal arm defines a tooth engaging surface.

15. The flow control device of claim 1 further comprising a pair of lateral arms extending from one of said first and second legs.

16. The flow control device of claim 15 said lateral arms are adjacent to said ramp.

17. A fluid processing set comprising: a container adapted for receiving biological fluid from a donor; a donor access device; a tubing segment defining a flow path that is in flow communication with said container and said access device; a flow control device associated with said tubing segment, said flow control device comprising: a flexible body comprising a central portion and first and second relatively movable legs extending from said central portion, said central portion including a window for receiving flexible tubing therethrough, said first and second legs being movable from a spaced apart position to a closed position; one of said first and second legs comprising at least a pair of substantially parallel terminal arms extending therefrom, said substantially parallel terminal arms defining a gap; the other of said first and second legs comprising a single terminal arm extending therefrom; wherein one of said pair of substantially parallel terminal arms includes a tooth having an engagement surface for engaging a surface on a tooth on said single terminal arm, wherein said engagement surface and a surface of said one of said pair of generally parallel arms from which said tooth extends forms an angle α of less than 90°; wherein said single terminal arm includes a tooth having an engagement surface that faces said engagement surface of said tooth on one of said pair of generally parallel terminal arms in said closed position, and wherein said engagement surface of said tooth on said single terminal arm and a surface from which said tooth on said single terminal arm extends form an angle α of less than 90°; at least one tube contacting member carried by one of said first and second legs for clamping said flexible tubing when said first and second legs are in a closed position; wherein the other of said first and second legs carries both (a) a tube contacting member for compressing the flexible tube when said first and second legs are in the closed position and (b) a ramp adjacent to said tube contacting member on the other of said of said first and second legs, said ramp comprising an ascending surface and a descending surface.

18. The fluid processing set of claim 17 further comprising:
   a second container for receiving biological fluid from said donor; and
   a second tubing segment defining a flow path between said second container and said access device.

19. A flow control device comprising: a flexible body comprising a central portion and first and second relatively movable legs extending from said central portion, said central portion including a window for receiving flexible tubing therethrough; one of said first and second legs comprising at least a pair of substantially parallel inner and outer arms extending from said one of said first and second legs and each terminating in a terminal tip end, said substantially parallel inner and outer arms defining a gap therebetween and wherein said substantially parallel inner arm is substantially shorter than said substantially parallel outer arm; the other of said first and second legs comprising an arm extending therefrom; wherein said substantially parallel inner arm of said pair of substantially parallel inner and outer arms includes a tooth projecting into said gap, and wherein said tooth is positioned on said substantially parallel inner arm closer to said terminal tip end than to the leg from which said substantially parallel inner arm extends; and wherein said single terminal arm includes a tooth having an engagement surface; wherein one of said first and second legs carries both (a) a tube contacting member for compressing said flexible tubing when said first and second legs are in a closed position and (b) a ramp adjacent to said tube contacting member on said one of said first and second legs, said ramp comprising an ascending surface and a descending surface.

20. The flow control device of claim 19 wherein said tooth on said inner arm is positioned at said terminal tip end.

21. The flow control device of claim 19 wherein a surface of said tooth on said substantially parallel inner arm and the a surface of said substantially parallel inner arm from which said tooth extends and which faces said gap form an angle α of less than 90°.

22. The flow control device of claim 21 wherein said angle α is at least 20°.

* * * * *